(12) United States Patent
Narasimhamoorthy et al.

(10) Patent No.: US 9,545,076 B2
(45) Date of Patent: Jan. 17, 2017

(54) SPEARMINT PLANT DENOMINATED KI-MSEM0042

(71) Applicant: Kemin Industries, Inc., Des Moines, IA (US)

(72) Inventors: Brindha Narasimhamoorthy, West Des Moines, IA (US); John A. Greaves, Ankeny, IA (US); Sarah Wildgen, Lawrence, KS (US); Rachel Barkley, Blair, NE (US); Susan Ruden, Dexter, IA (US)

(73) Assignee: Kemin Industries, Inc., Des Moines, IA (US)

( * ) Notice: Subject to any disclaimer, the term of this patent is extended or adjusted under 35 U.S.C. 154(b) by 0 days.

(21) Appl. No.: 14/203,097

(22) Filed: Mar. 10, 2014

(65) Prior Publication Data

US 2014/0208450 A1 Jul. 24, 2014

Related U.S. Application Data

(63) Continuation-in-part of application No. 13/367,863, filed on Feb. 7, 2012.

(60) Provisional application No. 61/440,558, filed on Feb. 8, 2011.

(51) Int. Cl.
*A01H 5/12* (2006.01)

(52) U.S. Cl.
CPC ...................................... *A01H 5/12* (2013.01)

(58) Field of Classification Search
None
See application file for complete search history.

(56) References Cited

U.S. PATENT DOCUMENTS

| | | |
|---|---|---|
| PP16,747 P3 | 7/2006 | Khanuja et al. |
| 2009/0260119 P1 | 10/2009 | Liu et al. |
| 2010/0137433 A1 | 6/2010 | Kott et al. |

FOREIGN PATENT DOCUMENTS

WO  WO 2008/090474  * 7/2008

OTHER PUBLICATIONS

Fletcher et al 2009, The Open Agriculture Journal 3: 43-49.*
Fletcher et al 2005A, Journal of the Science of Food and Agriculture 85: 2429-2436.*
Fletcher et al 2005B, Proc.3 WOCMAP III. vol. 6, Traditional Medicine and Nutraceuticals, ISHS Acta Hort. 680, pp. 31-36.*
Mazumder, Abhijit; Neamati, Nouri; Sunder, Sanjay; Schulz, Jutta; Pertz, Heinz; Eich, Eckart; Pommier, Yves, Curcumin Analogs with Altered Potencies against HIV-1 Integrase as Probes for Biochemical Mechanisms of Drug Action, Journal of Medical Chemistry, 1997, 40: 3057-3063.
Szabo, E.; Thelen, A.; Peterson, M.; Fungal elicitor preparations and methyl jasmonate enhance rosmarinic acid accumulation in suspension cultures of Coleus blumei, Plant Cell Reports, 1999, 18: 485-489.
Hooker, C.; Lott, William; Harrich, David; Inhibitors of Human Immunodeficiency Virus Type 1 Reverse Transcriptase Target Distinct Phases of Early Reverse Transcription, Journal of Virology, Apr. 2001, 3095-3104.
Wang, Huafu; Provan, Gordon; Helliwell, Keith; Determination of rosmarinic acid and caffeic acid in aromatic herbs by HPLC; Food Chemistry, 2004, 87: 307-311.
Kosar, Muberra; Dorman, H.J.; Baser, K.; Hiltunen, Raimo; Screening of Free Radical Scavenging Compounds in Water Extracts of Mentha Samples Using a Postcolumn Derivatization Method, Journal of Agriculture and Food Chemistry, 2004, 52, 5004-5010.
Fletcher, Ronald; Mcauley, Colette; Kott, Laima; Novel Mentha spicata Clones with Enhanced Rosmarinic Acid and Antioxidant Activity, WOCMAP III. vol. 6, Traditional Medicine and Nutraceuticals, 6S0, ISHS, pp. 31-40 SA-08-06337.
Fletcher, Ronald; Slimmon, Tannis; McAuley, Colette; Kott, Laima; Heat stress reduces the accumulation of rosmarinic acid and the total antioxidant capacity in spearmint (*Mentha spicata* L), Journal of the Science of Food and Agriculture, 85: 2429-2436.
Fletcher, Ronald; Slimmon Tannis; Kott, Laima; Environmental Factors Affecting the Accumulation of Rosmarinic Acid in Spearmint (*Mentha spicata* L.) and Peppermint (*Menta piperita* L.), The Open Agriculture Journal, 2009, 3, 43-49.

* cited by examiner

*Primary Examiner* — David H Kruse
(74) *Attorney, Agent, or Firm* — Davis, Brown, Koehn, Shors & Roberts, P.C.

(57) ABSTRACT

A new and distinct cultivar of *Mentha spicata* L. named KI-MsEM0042 and characterized by elevated levels of rosmarinic acid and vigorous growth.

15 Claims, 6 Drawing Sheets

SPEARMINT PLANT DENOMINATED KI-MSEM0042

This application is a continuation-in-part application of U.S. patent application Ser. No. 13/367,863, filed on Feb. 7, 2013, which claims priority to U.S. Patent Application Ser. No. 61/440,558, filed Feb. 8, 2011, which is incorporated herein in its entirety by this reference.

FIELD OF THE INVENTION

The present invention relates generally to a spearmint plant and, more specifically, to a plant of spearmint clonal line KI-MsEM0042 that produces a high amount of rosmarinic acid.

BACKGROUND OF THE INVENTION

Rosmarinic acid (RA) is an ester of caffeic acid and 3,4-dihydroxyphenylacetic acid. It is also a secondary metabolite of various plant species including those of Lamiaceae. Although rosmarinic acid was first extracted from rosemary (*Rosmarinus officinalis* L.), unlike the other abundant antioxidants compounds of rosemary (carnosic acid and carnosol), rosmarinic acid is more polar and appropriate for use in other food products. There is an interest in developing products based on the more polar rosmarinic acid that will likely have greater antioxidative efficacy in beverages, sauces, and emulsions. In addition, this molecule is known to have unique properties including antiviral, antibacterial, and anti-inflammatory activities (Mazumder A, Neamati N, Sunder S, Schulz J, Pertz H, Eich E, and Pommier Y. 1997. Curcumin analogs with altered potencies against HIV-1 integrase as probles for biochemical mechanisms of drug action. *Journal of Medical Chemistry.* 40:3057-3063; Szabo E, Thelen A and Paterson M. 1999. Fungal elicitor preparations and methyl jasmonate enhance rosmarinic acid accumulation in suspension cultures of *Coleus Blumei*. Plant Cell Reports 18: 485-489; Hooker C W, Lott W B and Harrich D. 2001. Inhibitors of human immunodeficiency virus Type 1 reverse transcriptase target distinct phases of early reverse transcription. *Journal Virology.* 75: 3095-3104).

Mint family species, including peppermint (*Mentha piperita* L.) and spearmint (*Mentha spicata* L.), are important specialty crops valued for the essential oils produced in trichomes on the surface of leaves. Spearmint is particularly known as a major source of carvone-rich essential oil for perfumery and flavoring industries and is grown worldwide. It is a fast-growing perennial crop that can biosynthesize significant amounts of rosmarinic acid and other phenolics. In addition, mint plants are capable of producing underground rhizomes which can be used as propagates for field planting. They are also capable of rapidly producing rooted branches which can aid in faster propagations. They are easy to cultivate, can sustain several harvests annually, and exhibits a rapid re-growth after each harvest.

While progressive genetic improvement was focused on increasing the essential oils, little or no effort has yet been made in the improvement of *M. spicata* for better production of rosmarinic acid or other antioxidant molecules. Today the major mint production areas of the United States, and even of the world, for the purpose of essential oils are found in the Columbia River basin, east of the mountains in Washington, Willamette Valley in Oregon, Michigan, and Indiana.

The reported levels of rosmarinic acid in *M. spicata* clones ranges from 7.1 to 14.3 mg/g dry weight (DW) basis (Wang H, Provan G J, Helliwell K. 2004. Determination of rosmarinic acid and caffeic acid in aromatic herbs by HPLC. *Food Chemistry,* 87:307-311; Kosar M, Dorman H J D, Baser K H C, Hiltunen R. 2004. Screening of free radical scavenging compounds in water extracts of *Mentha* samples using a postcolumn derivatization method. *Journal of Agricultural and Food Chemistry* 52(16): 5004-5010). However *M. spicata* clones biochemically selected in vitro for elevated levels of phenolics ranged from 20 to 67 mg/g DW (Fletcher R S, McAuley C and Kott L S. 2005a. Novel *Mentha Spicata* clones with enhanced rosmarinic acid and antioxidant activity. Proc. WOCMAP III, Vol. 6: *Traditional Medicine and Nutraceuticals Ada Horticulture*. 6S0, ISHS. pp 31-40 SA-08-06337; Fletcher R S, McAuley C and Kott L S. 2005b. Heat stress reduces the accumulation of rosmarinic acid and the antioxidant activity of Spearmint (*Mentha spicata* L.). *Journal of Science of Food and Agriculture* 85:2429-2436 SA-09-06343). One particular *M. spicata* clone, 700B (US Pat. Appl. 2010/0137433), selected in vitro, was found to produce 87 to 118 mg/g of rosmarinic acid on a DW basis. Rosmarinic acid levels are known to increase with light intensity, day length and optimal temperature (>70° F.) (Fletcher et al., 2005a). Extraction of rosmarinic acid from a hyper-accumulating spearmint variety is crucial for economically viable commercial rosmarinic acid production. Therefore developing spearmint varieties with high levels of rosmarinic acid combined with high biomass will provide an economically valuable rosmarinic acid source.

SUMMARY OF THE INVENTION

The invention consists of a plant of *Mentha spicata* L. named KI-MsEM0042 that has elevated rosmarinic acid levels, excellent vigor and overall agronomic robustness. The variety was propagated from seeds obtained from a commercial source of segregating spearmint. A plant with elevated levels of rosmarinic acid and good growth habits was selected and has been asexually propagated to produce a clonal line of identical plants.

Plants of the cultivar KI-MsEM0042 have not been observed under all possible environmental conditions. The phenotype may vary somewhat with variations in environment and culture such as temperature, light intensity, day length, water status, and/or fertilizer rate or type without, however, any variance in genotype.

An object of the present invention is a plant with a high level of rosmarinic acid for use as an antioxidant in human and animal food, beverages and personal care products.

Another object of the invention is a variety of spearmint that is novel, stable, and uniform and has good agronomic characteristics that permit efficient cultivation of the variety as a crop that produces a high amount of biomass from which rosmarinic acid can be extracted.

DETAILED DESCRIPTION OF THE INVENTION

Figure 1:
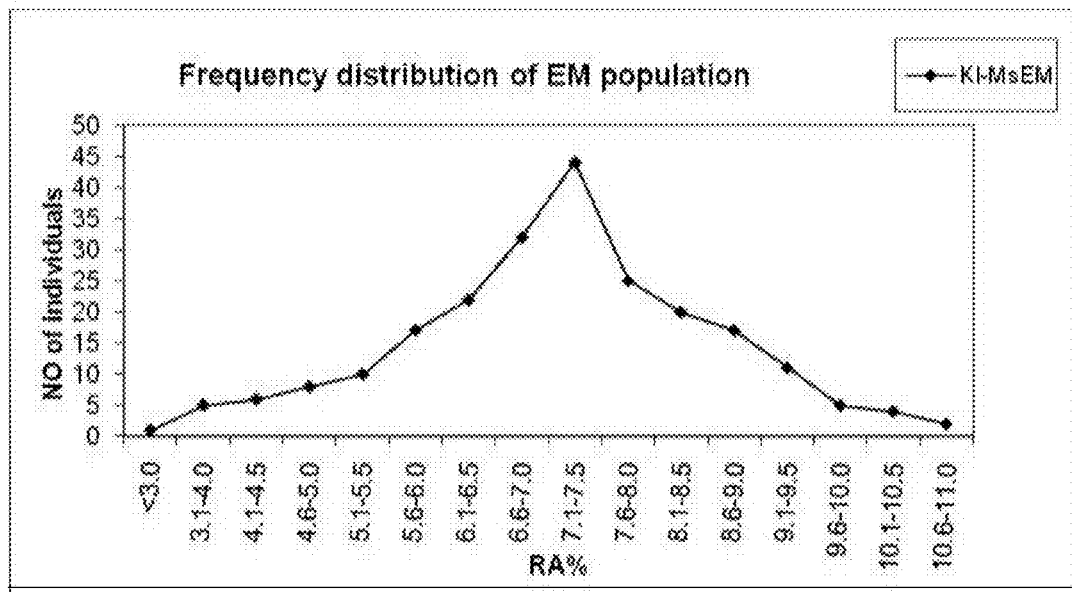
FIG. 1 is a chart of frequency distribution of the KI-MsEM population in comparison to KI-Ms0001.

The plants of the present invention have the taxonomic description of being genus Mentha, species spicata L., family Lamiaceae and the common name spearmint. Table 2 sets out a description of traits of the plants taken from plants growing in a greenhouse and Table 1 sets out the definitions of the traits of Table 2.

TABLE 1

| Description of the traits | |
| --- | --- |
| Days to first flowering | Number of days from transplanting to when you see the first spike/inflorescence |
| Days to 50% flowering | Number of days from transplanting to when you see 50% of branches have spikes |
| Days to 100% flowering | Number of days from transplanting to when you see 100% flowering |
| Plant height (cm) | Length of the middle stem at the time of flowering |
| Length of lateral branches (cm) | Length/Ht of the lateral stems |
| Number of lateral branches | Count the number of lateral branches |
| Number of nodes on $1^{st}$ flowering stem | Count the number of nodes on the stem that has the first inflorescence |
| Internode length on $1^{st}$ flowering stem | Measure the length between $5^{th}$ and $6^{th}$ internode of the flowering branch |
| Number of spikes per plant | Count the number of spikes per plant |
| Spike/flower color | Color of the flower petals when opened |
| Number of leaves per $1^{st}$ flowering stem | Count the number of leaves on the stem |
| Leaf width | Taken from $5^{th}$ leaf from top of the flowering stem |
| Leaf length | Taken from $5^{th}$ leaf from top of the flowering stem |
| Leaf area (cm$^2$) | Leaf width × Leaf length |

TABLE 1-continued

| Description of the traits | |
| --- | --- |
| Weight of aerial part of single plant (g) | Fresh and dry weight during 1st flowering |
| Leaf to stem ratio (can use the above plant) | Based on fresh weight during first flowering |
| RA levels | Taken from |
| Biomass or herbage yield/unit area from 1st harvest | Total biomass yield taken after $1^{st}$ harvest from unit area |
| Biomass or herbage yield/unit area from 2nd harvest | Total biomass yield taken after $2^{nd}$ harvest from unit area |
| Regrowth | Ability to grow back after harvest as a score |
| Ratio of suckers to aerial plant part | Sacrifice 2 whole plants from GH and field to do this; will be on fresh weight and dry weight basis |

TABLE 2

Characteristics of KI-MsEM0042 observed in the Maury Greenhouse

| | Average | Range |
| --- | --- | --- |
| Days to first flowering from date of transplanting rooted cuttings | 123 days | 121-125 days |
| Days to first flowering from date of taking cuttings for rooting | 130 days | 128-132 days |
| Plant height (cm) | 76.6 cm | 68.5-86.5 cm |
| Length of lateral branches (cm) | 56 cm | 51-61 cm |
| Number of lateral branches | 9 | 8-12 |
| Number of nodes on the $1^{st}$ flowering stem | 16 | 14-18 |
| Internode length on the $1^{st}$ flowering stem | 3.5 | 3.2-4.0 cm |
| Number of leaves per $1^{st}$ flowering branch | 66 | 52-86 |
| Leaf width taken from $5^{th}$ leaf from top of the flowering stem | 2.75 | 2.6-3 |
| Leaf length taken from $5^{th}$ leaf from top of the flowering stem | 5.0 | 4.8-5.5 |
| Leaf area (cm$^2$) taken from $5^{th}$ leaf from top of the flowering stem | 13.7 cm$^2$ | 12.9-15.6 cm$^2$ |
| Weight of aerial part of single plant (g) | 96.3 g | 88.5-110.5 g |
| Leaf to stem ratio | 0.65 | 0.58-0.72 |
| RA levels mg/g | 102.7 | 85.1-12.0 |

In an embodiment, the plant KI-MsEM0042 produces rosmarinic acid comprising greater than 8% dry weight rosmarinic acid and preferably greater than 10% dry weight rosmarinic acid.

The present invention is related to the development of a novel, stable, uniform vigorously growing robust mint plant KI-MsEM0042 of Mentha spicata L. This plant is unique and clearly distinct from all other existing varieties of Mentha spicata L. The Mentha spicata L. plant denominated KI-MsEM0042 as produced by a spearmint seed line deposited under the terms of the Budapest Treaty with the ATCC on Nov. 5, 2015 and assigned accession number PTA-122651.

Example 1

Selection and Development of Clonal Line

Materials and Methods

Plant Material. Seedlings of a population designated as KI-MsEM (230 genotypes) were developed from seeds obtained from independent commercial sources. Clones of line 700B (United States Patent Application 2010/0137433) designated as KI-Ms0001 were obtained from University of Guelph and used as a control. Line 700B clones along with the two populations were maintained in a greenhouse from January to May 2009 without supplemental illumination. The two populations and KI-Ms0001 (as a control) were planted in an unreplicated field trial at a central Iowa field nursery during May 2009.

Sample Preparation: Leaf tissue was collected from the top 8 cm of each plant. Leaf tissue from one randomly selected genotype of the population (KI-MsEMO219) and the KI-Ms0001 were collected after 4-6 weeks of establishment in the greenhouse. In addition leaf tissue from all the genotypes of both the populations and KI-Ms0001 established in the field was collected 4-6 weeks after transplanting. The KI-MsEM population samples were collected during the end of June. KI-Ms0001 that was grown as control was collected during both times. Leaf tissues were dried using the standard vegetable dehydrator (Open Country—Sportsman Kitchen) for 24-48 hrs.

Chemotyping: Dried leaves were ground manually using pestle and mortar. A rapid method for rosmarinic acid estimation using HPLC was used to determine rosmarinic acid levels. This method is rapid with high-resolution, low-detection-limit, and uses quantitative reversed phase HPLC/DAD which was developed specifically for the rapid screening of several hundred spearmint genotypes. All the field grown 230 genotypes of the KI-MsEM population were screened along with field KI-Ms0001 were screened using the same method. The population was compared to rosmarinic acid levels present in KI-Ms0001.

Data analysis: Statistical analysis was performed on all data from each population separately using Statgraphics Centurion XV to determine the significant differences. Rosmarinic acid levels were analyzed by one way analysis of variance. Fisher's least significant difference (LSD) to discriminate the means was computed using multiple range tests to select the significantly high rosmarinic acid producing genotypes.

Results

Plant materials: KI-Ms0001 is a patent pending rosmarinic acid hyper-accumulating spearmint line developed by University of Guelph. Under license, seedlings generated from the commercial seeds were established in the greenhouse for the purpose of comparing with KI-Ms0001. These seedlings were maintained in small pots in the greenhouse and the plants exhibited few morphological differences. However, when they were transplanted in the field location, these genotypes showed a tremendous amount of variation in leaf color, shape, and growth as they developed.

Rosmarinic acid levels of spearmint grown in greenhouse vs. field. Leaf tissue samples from one genotype from the population (KI-MsEMO219) and KI-Ms0001 that were grown in greenhouse were collected during March 2009. The rosmarinic acid accumulated in KI-MsEMO219 (27.7 mg/g) was higher than KI-Ms0001 (14.8 mg/g) during March while growing in the greenhouse. The same genotypes were grown in the field and tested for their rosmarinic acid levels during June. Both proprietary genotypes accumulated three to four times' higher levels of rosmarinic acid when grown in the field as compared to being grown under greenhouse conditions. KI-MsEMO219 accumulated the highest levels of rosmarinic acid (92.2 mg/g) compared to KI-Ms0001 (68 m/g).

Rosmarinic acid levels of KI-MsEM population. All the field grown 230 genotypes of this population along with KI-Ms0001 were analyzed for rosmarinic acid content during June. Significant variation (p<0.0001) was observed among all 230 genotypes for the rosmarinic acid levels. Rosmarinic acid content ranged from 29.5 mg/g to 108.9 mg/g among all the genotypes of this population. The mean rosmarinic acid content of from 20 clones (which are genetically identical) KI-Ms0001 was 70.8 mg/g DW and that of the population was 71.1 mg/g DW (Table 1). Twenty genotypes from this population had significantly higher levels of rosmarinic acid content (>2 LSD) compared to KI-Ms0001. KI-MsEM110 (108.9 mg/g) and KI-MsEM42 (108.4 mg/g) accumulated the highest amounts of rosmarinic acid showing 50% improvement over KI-Ms0001. There were at least six genotypes that accumulated more than 100 mg/g of rosmarinic acid.

TABLE 3

Means, ranges, and LSD in KI-MsEM population.

|  | KI-MsEM population |
|---|---|
| Range of the population | 29.5-108.9 mg/g |
| Mean of the population | 71.1 mg/g |
| LSD | 10.1 |
| Mean of KI-Ms0001 | 70.8 mg/g |

Frequency distribution of the populations. The frequency distribution of the populations in comaprison with the KI-Ms0001 is given in FIG. 1. The mean of the KI-MsEM population (71.1 mg/g) was very similar to KI-Ms0001 (71.3 mg/g).

Discussion

Clonal lines of spearmint specifically selected for high rosmarinic acid levels provide an inexpensive biomass source for this antioxidant molecule. It has been reported that typical wild type or naturally existing spearmint produces only about 5 mg/g DW (U.S. Pat. Appl. 2010/0137433). Researchers at University of Guelph developed a patent pending rosmarinic acid hyper-accumulating spearmint line using an in vitro screening technique. In this process spearmint seeds were soaked in an inhibitor (L-α-bromophenylalanine) of the primary enzyme in the phenylpropanoid pathway (U.S. Pat. Appl. 2010/0137433). According to U.S. Pat. Appl. 2010/0137433, this resulted in only plants that were capable of high rosmarinic acid accumulation or plants that convert rosmarinic acid to other intermediates. Among several plants that showed high levels of rosmarinic acid, line 700B (KI-Ms0001) was selected which showed stable rosmarinic acid levels (>70 mg/g DW) combined with desirable agronomic properties. A research license to this line was obtained with an intention of confirming the stable production of rosmarinic acid and as a reference control for the development of proprietary lines.

The independent field grown segregating spearmint population (KI-MsEM) were tested for rosmarinic acid levels in comparison to KI-Ms0001. It was anticipated that KI-Ms0001 would accumulate the highest levels of rosmarinic acid compared to the individuals of both the populations. However, our evaluations identified at least 31 spearmint lines from both the populations showing significantly higher levels of rosmarinic acid compared to KI-Ms0001. Of these at least seven genotypes showed rosmarinic acid levels higher than 100 mg/g and three of the genotypes showed >50% increase in rosmarinic acid levels over KI-Ms0001. The mean of the two populations were similar to the control KI-Ms0001.

The outcome of this study, although unexpected, suggests that spearmint is capable of accumulating higher levels of rosmarinic acid in nature and they were able to be identified without enzyme inhibiting in vitro screening.

The rosmarinic acid levels from the field grown material was three to four times higher than the greenhouse grown material. The biosynthesis of rosmarinic acid is dependent upon plant maturity, temperature, and light intensity. Rosmarinic acid levels would be expected to increase with light intensity and optimal temperature. Fletcher et al., (2005a) showed that rosmarinic acid levels of hyper-accumulating spearmint lines were found to increase during July and August (pre-flowering, vegetative stage) and decrease during October under field conditions in Canada, post flowering. The seedlings of the population (KI-MsEM) and young propagates from clones of KI-Ms0001 were grown at the Maury campus greenhouse from January to March, 2009 without supplemental illumination. This material when tested in March was expected to show lower rosmarinic acid levels. Upon exposure to higher light levels and longer day lengths under field conditions, the rosmarinic acid levels increased significantly (about 4 times).

*M. spicata* is self-incompatible and is thus an out-crossing plant, generally requiring cross-pollination of differing genotypes with a very low percentage of seed set through self-pollination. New segregating spearmint populations will be created through half sib or full sib crosses between the selected high rosmarinic acid lines with desirable agronomic characters. It is anticipated that the recombinants created via crossing between selected genotypes can create new desirable variation via random allelic combinations for further increased rosmarinic acid content.

Example 2

Field Trial

In early May, propogules of spearmint variety KI-MsEM0042 and check variety KI-Ms0001 were planted in a field of sandy muck soil in Indiana comprising 3 acres and 2 acres, respectively. Normal mint horticultural practices were maintained by farmers experienced in growing commercial varieties of spearmint.

Figure 2:
FIG. 2 shows rows of plants of the variety KI-MsEM0042 in mid-June that were planted in early May.

In mid-June, plants of both varieties had established very well (FIG. 2) and were already starting to send out surface runners along with underground rhizomes. The new clonal line KI-MsEM0042 was clearly more vigorous than the check variety KI-Ms0001. Many of the plants were also showing pre-flowering signs and some of the plants were flowering while others had not yet flowered. In order to retard the plants and keep them in a vegetative state, the plants were "topped" by cutting the uppermost 2 inches of growth. This removed most of the flowering heads and maintained the plants in a vegetative state.

Figure 3:
FIG. 3 shows rows of plants of the variety KI-MsEM0042 in late June wherein the center, taller rows were planted in early May and the right, shorter rows were planted in early June.

In late June, the plants had completely re-grown and looked excellent. KI-MsEM0042 continued to be significantly more vigorous and consistent than KI-Ms0001. The regrowth from the cut taken in mid-June was surprising. Rows of two plantings of KI-MsEM0042 are shown in FIG. 3 (early May in the center, early June on the right).

Figure 4:
FIG. 4 shows rows of plants of the variety KI-MsEM0042 in late July that were planted in early May.
Figure 5:
FIG. 5 shows rows of plants of the variety KI-MsEM0042 in early to mid-August at the time of harvest.
Figure 6:
FIG. 6 shows a section of a row of plants of the variety KI-MsEM0042 in mid-season.
Figure 7:
FIG. 7 shows the initial spike of a plant of the variety KI-MsEM0042.
Figure 8:
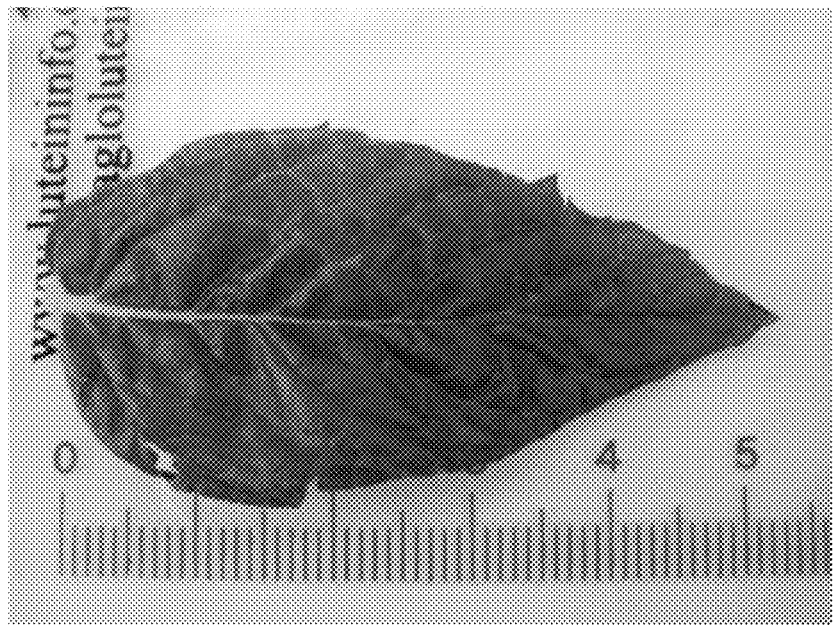
FIG. 8 shows the length of a leaf of a plant of the variety KI-MsEM0042 against a centimeter scale.
Figure 9:
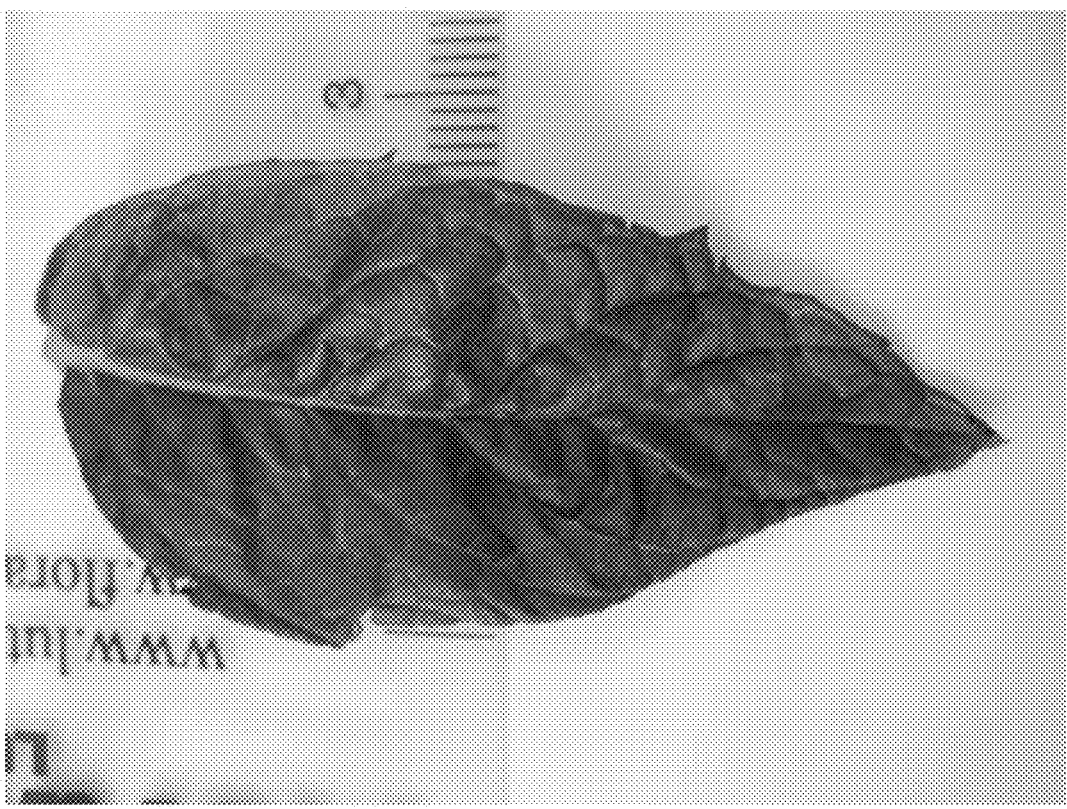
FIG. 9 shows the width of a leaf of a plant of the variety KI-MsEM0042 against a centimeter scale.

In late July, the plants of both varieties had been topped again to discourage flowering and increase biomass yield (FIG. 4). KI-MsEM0042 continued to be significantly more vigorous and consistent than KI-Ms0001.

Evidence of Uniformity and Stability

No variants of any kind have been observed since the variety KI-MsEM0042 was identified, indicating the stability and uniformity of the genotype. It is clear from these results that the KI-MsEM0042 cultivar is stable and reproduces true to type in successive generations of asexual reproduction.

Statement of Distinction

KI-MsEM0042 is more vigorous and generates more biomass per acre than 700B (KI-Ms0001 and consistently produces higher per dry weight levels of rosmarinic acid. Due to vigorous vegetative growth this genotype can be harvested multiple times in a season and has the potential of growing in any temperate climate.

Example 3

Sequence Information

A DNA sample from KI-MsEM0042 extracted from tissue was sequenced by Data2Bio, LLC (Ames, Iowa) in two Ilumina HiSeq 2000 paired-end (PE) lanes (lanes 3 and 4). Each genomic DNA sample was prepared using the Illumina protocol outlined in "TruSeq DNA Sample Preparation Guide" (Catalog# PE-940-2001). First, gDNA was fragmented (Covaris Sheraing duration time 120 sec) to produce 300-400 bp inserts. The DNA fragment ends were repaired and phosphorylated using Klenow, T4 DNA polymerase and T4 polynucleotide kinase. Next, an "A" base was added to the 3' end of the blunted fragments, followed by ligation of Illumina adapters via T-A mediated ligation. The ligated products were size selected by AMPure XP Beads and then PCR amplified using Illumina primers. The library size and concentration were determined using an Agilent Bioanalyzer 1000 chip. Raw reads from both lanes were combined into a single archive and summarized in Table 4.

TABLE 4

Summary of Raw Sequence Reads

| | RAW READS | | |
|---|---|---|---|
| File Name | No. Reads | Base Pairs | Read Length (BP) |
| KI-42_1.fastq | 359,477,547 | 36,307,232,247 | 101 |
| KI-42_2.fastq | 359,477,547 | 36,307,232,247 | 101 |
| KI-42 Total | 718,955,094 | 72,614,464,494 | 101 |

The nucleotides of each raw read were scanned for low quality. Bases with PHRED quality value <15 (out of 40) (Ewing, B. and P. Green, 1998. Base-calling of automated sequencer traces using phred. II. Error probabilities. *Genome Res.* 8(3): 186-194), i.e., error rates of <0.03%, were removed by the trimming pipeline. Each read was examined in two phases. In the first phase reads were scanned starting at each end and nucleotides with quality values lower than the threshold were removed. The remaining nucleotides were then scanned using overlapping windows of 10 bp and sequences beyond the last window with average quality value less than the specified threshold were truncated. The trimming parameters were referred to the trimming software, Lucy (Chou, H. H., G. Sutton, A. Glodek and J. Scott, 1998 Lucy—A Sequence Cleanup Program, pp. in *Proceedings of the Tenth Annual Genome Sequencing and Annotation Conference (GSAC X)*, Miami, Fla.). A statistical summary of raw reads is shown in Table 5.

TABLE 5

Summary of Raw Reads Trimming

| | RAW READS | | |
|---|---|---|---|
| File Name | No. Reads | Base Pairs | Read Length (BP) |
| KI-42_1.fastq | 359,477,547 | 36,307,232,247 | 101 |
| KI-42_2.fastq | 359,477,547 | 36,307,232,247 | 101 |

TABLE 5-continued

Summary of Raw Reads Trimming

| | | | |
|---|---|---|---|
| KI-42 Total | 718,955,094 | 72,614,464,494 | 101 |

TRIMMED READS

| File Name | No. Reads (%, trimmed/raw) | Base Pairs (%, trimmed/raw) | Read Length (BP) |
|---|---|---|---|
| KI-42_1.fastq | 357,712,544 (99.5%) | 34,443,035,333 (94.9%) | 97 |
| KI-42_2.fastq | 352,515,743 (98.1%) | 33,739,652,728 (92.9%) | 96 |
| KI-42 Total | 710,228,287 (98.8%) | 68,182,688,061 (93.9%) | 97 |

The raw sequences have been deposited and uploaded to the Sequence Read Archive (SRA) database of the National Center for Biotechnology Information (NCBI), U.S. National Library of Medicine, Bethesda, Md., and those sequences are incorporated herein in their entirety by this reference. The submission accession assigned by NCBI is SRA049735-SRS290758 and it was released to the public on Feb. 7, 2012. Those skilled in the art can analyze the deposited raw sequence information to determine the genetic sequence of KI-MsEM0042.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

We claim:

1. A method of extracting rosmarinic acid, comprising extracting rosmarinic acid from plant tissue of a spearmint *Mentha spicata* L. plant denominated KI-MsEM0042 as produced by a spearmint line deposited with the ATCC and assigned accession number PTA-122651.

2. The method of claim 1, wherein the plant tissue is selected from the group consisting of leaf, rhizome, root, seed, or stem tissue.

3. The method of claim 1, further comprising: utilizing the rosmarinic acid as an antioxidant in a product selected from the group consisting of: human food, animal food, beverages and personal care products.

4. The method of claim 3, further comprising drying the plant in a vegetable dehydrator.

5. The method of claim 4, wherein the plant is field grown, and further comprising topping the plant to remove flowering heads at least once.

6. A method of providing an antioxidant, comprising extracting rosmarinic acid from plant tissue of a spearmint *Mentha spicata* L. plant denominated KI-MsEM0042 as produced by a spearmint line deposited with the ATCC and assigned accession number PTA-122651.

7. The method of claim 6, wherein the antioxidant is included in product selected from the group consisting of: human food, animal food, beverages and personal care products.

8. The method of claim 7, further comprising drying the plant tissue in a vegetable dehydrator.

9. A method of providing an antioxidant, comprising:
   a. field growing plant tissue of a spearmint *Mentha spicata* L. plant denominated KI-MsEM0042 as produced by a spearmint line deposited with the ATCC and assigned accession number PTA-122651;
   b. harvesting the plant tissue;
   c. extracting rosmarinic acid from the plant tissue; and
   d. utilizing the rosmarinic acid in a product.

10. The method of claim 9, wherein the tissue is selected from the group consisting of leaf, rhizome, root, seed, or stem tissue.

11. The method of claim 9, wherein the antioxidant product is selected from the group consisting of: human food, animal food, beverages and personal care products.

12. The method of claim 11, wherein the plant tissue is field grown, and further comprising topping the plant to remove flowering heads at least once.

13. The method of claim 11, further comprising drying the plant tissue in a vegetable dehydrator.

14. The method of claim 11, wherein the spearmint plant is field grown, and further comprising:
   a. topping the spearmint plant to remove flowering heads at least once; and
   b. drying the spearmint plant tissue in a vegetable dehydrator.

15. The method of claim 14, wherein the plant tissue comprises greater than 80 mg/g rosmarinic acid on a dry weight basis after drying.

* * * * *